United States Patent
Gilligan et al.

(10) Patent No.: US 11,144,188 B1
(45) Date of Patent: Oct. 12, 2021

(54) DRAG AND DROP TO HIGHLIGHT AND TRANSFER DATA

(71) Applicant: ALLSCRIPTS SOFTWARE, LLC, Chicago, IL (US)

(72) Inventors: Patrick S. Gilligan, Raleigh, NC (US); Ross C. Teague, Cary, NC (US)

(73) Assignee: Allscripts Software, LLC, Chicago, IL (US)

( * ) Notice: Subject to any disclaimer, the term of this patent is extended or adjusted under 35 U.S.C. 154(b) by 0 days.

(21) Appl. No.: 16/425,788

(22) Filed: May 29, 2019

(51) Int. Cl.
*G06F 3/0486* (2013.01)
*G06F 3/0482* (2013.01)
*G06F 3/0481* (2013.01)
*G16H 10/60* (2018.01)

(52) U.S. Cl.
CPC .......... *G06F 3/0486* (2013.01); *G06F 3/0482* (2013.01); *G06F 3/04817* (2013.01); *G16H 10/60* (2018.01)

(58) Field of Classification Search
CPC .... G06F 3/0486; G06F 3/0481; G06F 3/0482; G16H 10/60
See application file for complete search history.

(56) References Cited

U.S. PATENT DOCUMENTS

| | | |
|---|---|---|
| 2013/0290032 A1* | 10/2013 Netsch | G06Q 50/24 705/3 |
| 2016/0026773 A1* | 1/2016 Chu | A61J 7/02 705/2 |
| 2017/0230453 A1* | 8/2017 Verma | H04N 21/23 |

* cited by examiner

*Primary Examiner* — Andrea C Leggett
(74) *Attorney, Agent, or Firm* — Loza & Loza, LLP; Peter Zura

(57) ABSTRACT

Electronic messages, such as emails, often ask questions, ask that a task be done, or assign a task. The responsive messages often forget to answer the questions and the responders often forget to calendar tasks. Advances in natural language processing provide computers the ability to notice the questions and task requests/assignments. Automated analysis of the messages can detect and highlight questions, can provide for draft responses addressing every question, and can provide for getting tasks calendared.

20 Claims, 12 Drawing Sheets

DRAG AND DROP TO HIGHLIGHT AND TRANSFER DATA

TECHNICAL FIELD

Embodiments relate to electronic health records, electronic messaging, and graphical user interfaces. More specifically, the embodiments relate to improvements in systems and methods for ensuring the review of noteworthy medical information.

BACKGROUND

Patients often see a number of health care providers, even during a single visit to a doctor's office. Each of those health care providers observes the patient, often taking data. For example, a medical assistant often performs the initial intake and takes the patients pulse, blood pressure, temperature, and other information. From there, a nurse may observe the patient and obtain even more information. Eventually, the patient may be seen by a physician who goes over the patient's chart, my diagnose ailments, and may prescribe medicine. The medical assistant and the nurse may have observed something noteworthy that they want the physician to pay attention to. They may write a note to the doctor, write on the patient's chart, or in some other manner attempt to convey the information to the physician. These attempts often fail and may result in the patient receiving poor health care.

The attempts to direct the physician's attention to noteworthy information may fail because notes get lost, notes on the patient's chart go unnoticed, or some other communications failure may occur. Communications failures are not due to lack of effort or lack of attention. Doctors and other clinicians spend a lot of time looking through notes and clicking around an interface to see if there is anything important they need to see.

Electronic health records (EHRs) are a recent advance in health care. An electronic health record (EHR) is a digital version of a patient's paper chart. EHRs are real-time, patient-centered records that make information available instantly and securely to authorized users. An EHR can contain the medical and treatment histories of patients. Specifically, an EHR can contain a patient's medical history, diagnoses, medications, treatment plans, immunization dates, allergies, radiology images, and laboratory and test results.

Even though EHRs provide for a great deal of information sharing, attempts to direct the physician's attention to noteworthy information may fail. Systems and methods that overcome the current limitations of paper notes, paper charts, word of mouth, and current generation EHRs are needed.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

The herein disclosed systems and methods for directing a physician's attention to specific information via graphical user interfaces and a drag and drop paradigm are significant advances over the prior art and in particular over paper-based methods and word of mouth. These systems and methods are advances because the information is difficult to lose and the physician's attention is drawn directly to the information without requiring intervention or attention from other people who may have moved on to other patients, gone home, or been called to an emergency. The disclosed embodiments reduce the burden on clinicians to find the information and provide the added benefit of peace of mind that the important information has been seen.

It is therefore an aspect of the embodiments to mark a datum of an electronic health record for later review. A method for marking a datum of an electronic health record for later review can include associating a datum alert with the datum. The datum can be marked by a first person for review by a second person. The first person can be a medical assistant (MA) or nurse. The second person can be a physician, a.k.a doctor. A graphical user interface (GUI) can be provided to a MA. The GUI can present an EHR and a collection icon. Presenting an EHR does not necessarily mean presenting every piece of data in the EHR. For example, presenting the EHR can mean presenting intake data for a particular visit to a doctor's office or presenting a set of lab test results.

It is another aspect of the embodiments to accept a datum selection. The datum has been presented to the MA in the GUI as a part of the EHR. The GUI having presented the datum as part of the electronic health record of a patient, the datum is selectable. The MA may have just entered the datum into the GUI. The datum, having been entered, is now being presented by the GUI. The first person can select the GUI by a number of GUI interactions including by touching the datum with a touch screen detecting the touch or by pressing a mouse button when a GUI cursor is over the datum. Those experienced with using computers, tablet computers, and smart phones are also experienced with these and various other ways of selecting an item presented by a GUI.

It is a further aspect of the embodiments to detect dragging the datum toward the collection icon. Detecting a datum drag can include detecting that a person who selected the datum by touching a touch screen is moving their finger on the touch screen. Detecting a datum drag can also include detecting that a person touched who selected the datum by pressing a mouse button is moving the mouse without releasing the mouse button.

It is yet another aspect of the embodiments to signal that releasing the datum will associate a datum alert with the datum. For example, dragging the datum over the collection icon can cause signaling wherein the collection icon becomes highlighted by changing color, by flashing, or by otherwise changing appearance. Dragging the datum all the way to the collection icon and dropping it directly on the collection icon may be difficult in many situations. Therefor, dragging the datum near the collection icon may be sufficient. For example, dragging the datum to within a collection range, which can be a predefined non-zero distance, may be sufficient. The distance between the dragged datum and the collection icon can be detected. When the distance is small enough, the GUI can provide a signal that releasing the datum will associate a datum alert with the datum.

It is a yet further aspect to detect a datum release. Those familiar with GUIs will recognize that the datum is being dragged and dropped. Drag and drop can have three stages: selecting, dragging, and releasing. Selection and dragging are discussed above. Those familiar with GUIs are also familiar with releasing a dragged item by releasing a mouse button, lifting a finger from a touch screen, and other actions. Upon detecting the datum release, the distance between the release point and the collection icon. The release point is the location where the datum was released. If the distance is less than the collection range then a datum alert is associated with the datum.

It is still another aspect of the embodiments to inform a second person, such as a physician, of the datum alerts. The physician can be informed by providing an indicator to the physician that there are datum alerts. The indicator can indicate a count of the datum alerts. For example, if there are three datum alerts for the physician, then the count is three. The number of datum alerts can be indicated by showing a number on the indicator. For example, the indicator can be the collection icon or another icon and a superimposed number. The datum alert can be presented to the physician. The datum alert can be presented in an EHR context. Presenting in an EHR context necessitates presenting an EHR. For example, the earlier described GUI presents an EHR. Presenting in an EHR context can be presenting a GUI showing an EHR and focused on, centered on, navigated to, or otherwise highlighting the datum alert or the datum associated with the datum alert.

The indicator has the advantage of showing that there are datum alerts without the indicator being lost or hard to notice amongst visual clutter. An EHR presentation can provide a lot of information in a small space, leading to visual noise. Highlighting a datum can add to the visual noise or the highlighting can be hard to notice. For example, adding an icon next to a bit of data that the MA wants to make note of can result in visual noise and an unnoticed icon. The drag and drop paradigm described herein mitigates the problem of visual noise in that dragging to a certain place, the collection icon, keeps the interface clean. The dragging and dropping paradigm also gives the user a sense of place and reinforces that they are moving data (without actually moving it) to a place that others can see.

Having considered the datum alert, the physician may want to clear it and proceed to another datum alert or some other duty. The datum alert can be cleared after accepting a datum alert dismissal. Deletion of the datum alert from a database or storage is one way of clearing the datum alert. Another way of clearing of the datum alert is to set a flag or status bit indicating that the datum has been cleared.

The physician can be informed of the datum alerts while observing the same GUI as that used by the MA to create the datum alerts. When providing the physician with the GUI, the GUI presents the EHR and the collection icon. The collection icon can be the indicator indicating the number of collection alerts. A number appearing in or on the collection icon can indicate the number of datum alerts. Here, the MA would also be informed of the number of datum alerts with the number incrementing each time a datum alert is associated with a datum. The number decreases each time a datum alert is cleared.

Selecting the indicator can cause a list of datum alerts to be presented. Selecting a datum alert on the list can cause the EHR to be displayed and focused on, centered on, navigated to, or otherwise highlighting the datum or datum alert. Datum alerts can be presented in a number of ways. For example, a datum alert can be presented when shown in a list of datum alerts. A datum alert can be presented by presenting an EHR and highlighting the datum associated with the datum alert.

The permissions of the MA and the physician can control that person's ability to set and clear datum alerts. A person can be required to log into or otherwise authenticate themselves with a device before the device presents the GUI. The authentication process can establish if a person is permitted to set datum alerts or to clear datum alerts. A person having permission to set datum alerts for a particular patient's EHR can associate datum alerts with such datums. A person having permission to clear datum alerts for a particular patient's EHR can clear such datum alerts. For tracking purposes, events involving datum alerts can be logged. Those familiar with managing computers are familiar with log files and other ways of logging events. The logged events can include setting a datum alert, clearing a datum alert, or any modification of a datum alert.

Some datum alerts are more severe than others. For example, a datum alert can relate to something that is critical, urgent, high priority, or low priority. Displaying a severity selection graphic upon detecting the datum release (the drop part of drag and drop) provides for the MA to select a severity level of the datum alert. Upon receiving the MA's severity level selection, associating the severity level with the datum alert can save the severity level selection for later presentation to the physician. The indicator, which indicates a count of datum alerts to the physician, can also indicate the severity level of the datum alert having the highest severity level. The severity levels are ranked from highest to lowest. The higher the severity level, the more important it is for the physician to review the datum alert.

A display device can show the GUI to the MA and the physician and an input device can accept inputs from the MA and the physician. The EHR and the collection icon are seen on the display device. A datum selection, a drag, and a datum release are examples of inputs received by the input device. A processor operatively coupled to the display device and the input device can cause the GUI to be presented and can process inputs from the input device. A memory operatively coupled to the processor can store EHRs and datum alerts. An application module can store one or more executable applications such as an application using a drag and drop methodology to create datum alerts. The processor can be configured to detect the datum drag of the datum toward the collection icon which causes the display device to signal that releasing the datum will associate a datum alert with the datum, and to associate the datum alert with the datum in response a datum release.

The processor can also be configured to provide the indicator indicating there is at least one datum alert to the physician, to cause the display device to present datum alerts to the physician, and to clear datum alerts in response to accepting datum alert dismissals.

Furthermore, the processor can be configured to, upon detecting a datum release, cause the GUI to display a severity selection graphic that provides for selecting a severity level for the datum alert and to associate datum alerts with the severity levels.

These and other features and advantages of the disclosed embodiments will be presented in more detail in the following specification and the accompanying figures, which illustrate by way of example the principles of the disclosed embodiments.

BRIEF DESCRIPTION OF THE DRAWINGS

The accompanying figures, in which like reference numerals refer to identical or functionally similar elements throughout the separate views and which are incorporated in and form a part of the specification, further illustrate the present invention and, together with the background of the present invention, brief summary of the invention, and detailed description of the invention, serve to explain the principles of the present invention.

DETAILED DESCRIPTION

Figure 1:
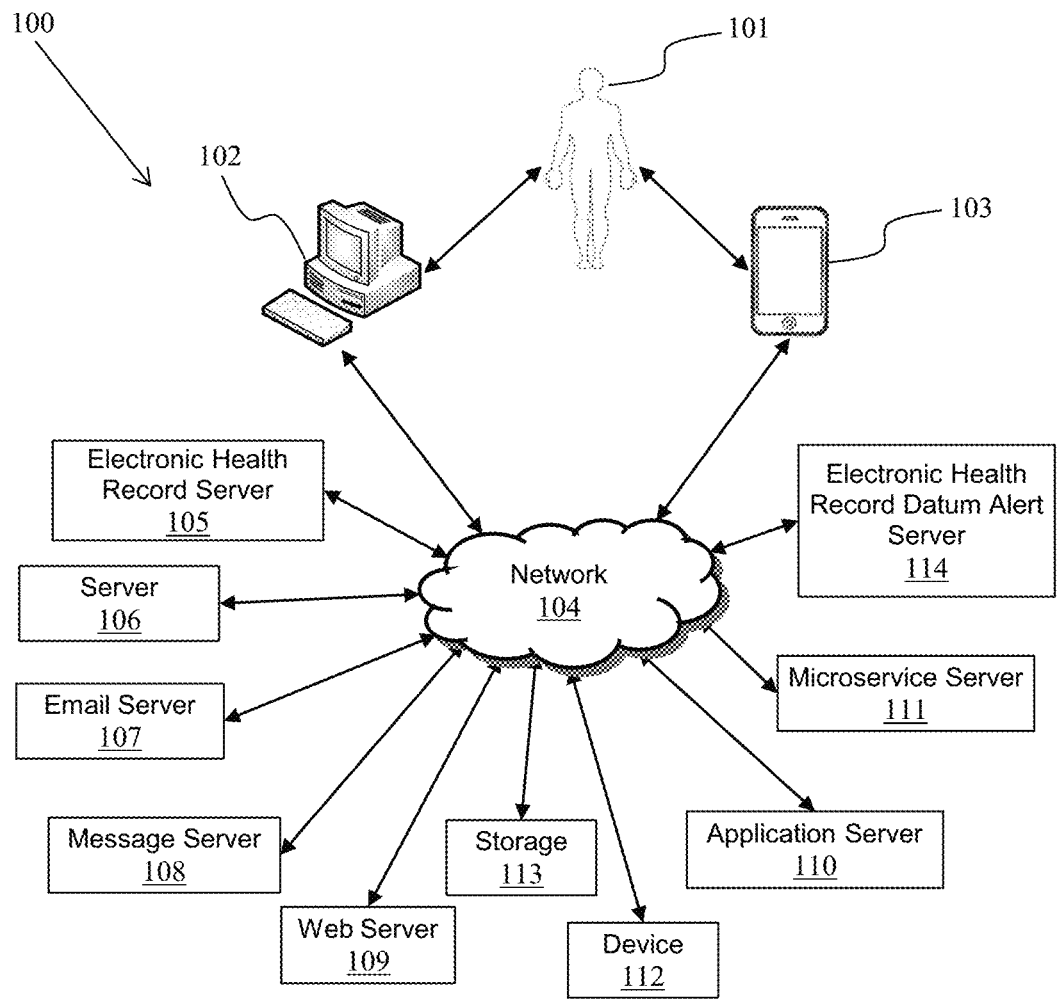
FIG. 1 illustrates a computing environment with a person interacting with devices to view EHRs, set datum alerts, and clear datum alerts in accordance with aspects of the embodiments.

The particular values and configurations discussed in the following non-limiting examples can be varied and are cited merely to illustrate one or more embodiments and are not intended to limit the scope thereof.

Example embodiments will now be described more fully hereinafter with reference to the accompanying drawings, in which illustrative embodiments are shown. The embodiments disclosed herein can be embodied in many different forms and should not be construed as limited to the embodiments set forth herein; rather, these embodiments are provided so that this disclosure will be thorough and complete, and will fully convey the scope of the embodiments to those skilled in the art. Like numbers refer to like elements throughout.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It is contemplated that any embodiment discussed in this specification can be implemented with respect to any method, kit, system, or instantiation of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize or be able to ascertain using no more than routine experimentation, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements, or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

All of the systems and/or methods disclosed and claimed herein can be made and executed without undue experimentation in light of the present disclosure. While the compositions and methods of this invention have been described in terms of preferred embodiments, it will be apparent to those skilled in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Figure 2:
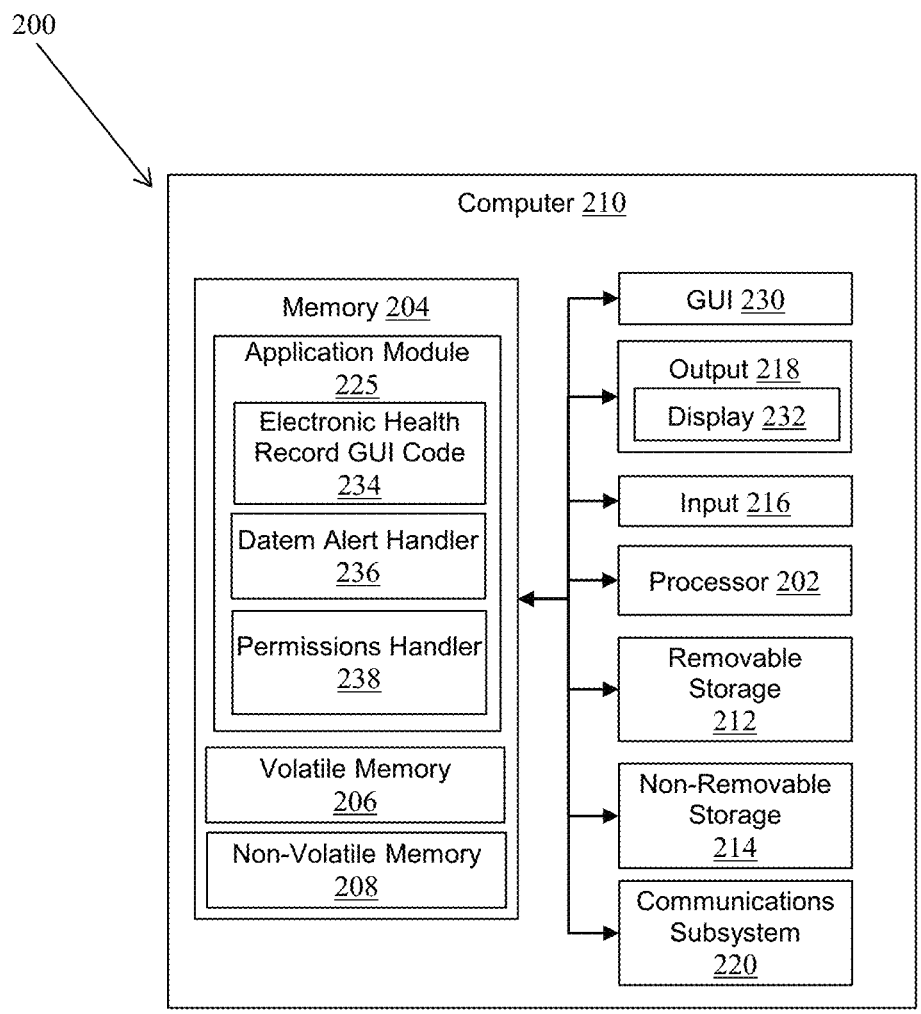
FIG. 2 depicts a block diagram of a computer system which is implemented in accordance with the disclosed embodiments.
Figure 3:
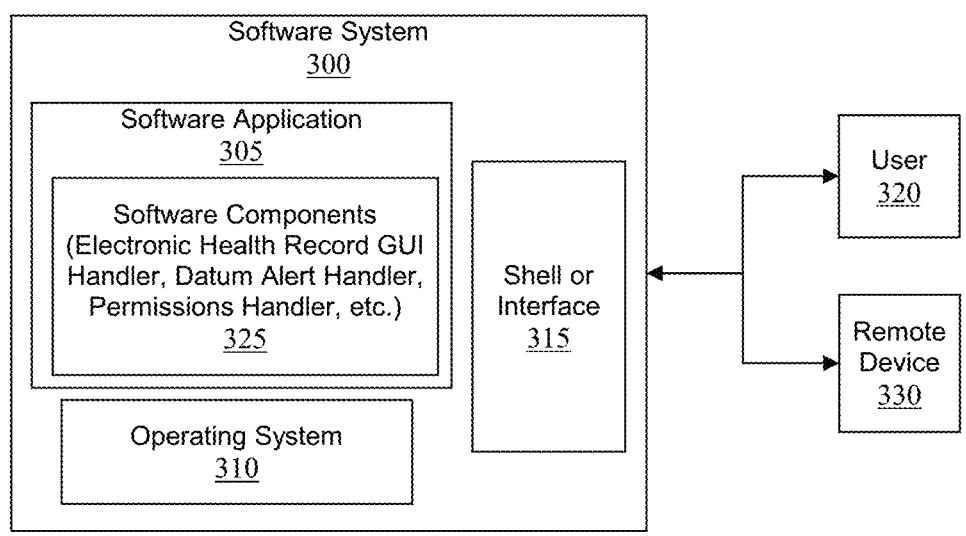
FIG. 3 depicts a computer software system for directing the operation of the data-processing system depicted in FIG. 2 in accordance with an example embodiment.

FIGS. 1-3 are provided as exemplary diagrams of data-processing environments in which embodiments of the present invention may be implemented. It should be appreciated that FIGS. 1-3 are only exemplary and are not intended to assert or imply any limitation with regard to the environments in which aspects or embodiments of the disclosed embodiments may be implemented. Many modifications to the depicted environments may be made without departing from the spirit and scope of the disclosed embodiments.

FIG. 1 depicts a graphical representation of a network of data-processing systems 100 in which aspects of the present invention may be implemented. Network data-processing system 100 can be a network of computers or other such devices, such as mobile phones, smartphones, sensors, controllers, speakers, tactile devices, and the like, in which embodiments of the present invention may be implemented. Note that the system 100 can be implemented in the context of a software code such as that in application module 203. The system 100 includes a network 104 in communication with one or more client devices such as desktop computer 102 and smart phone 103. Network 104 may also be in communication with one or more devices 112, servers 105-111 and 114, and storage 113. Network 104 is a medium that can be used to provide communications links between various devices and computers connected together within a networked data processing system such as computer system 200. Network 104 may include connections such as wired communication links, wireless communication links of various types, and fiber optic cables. Network 104 can communicate with one or more servers 105-111 and 114, one or more external devices such as device 112, and a memory storage unit such as, for example, memory or database 113. It should be understood that device 112 may be embodied as networked equipment such as a robot, printer, scanner, or other device that measures or manipulates physical objects.

In the depicted example, device 112, servers 105-111 and 114, and client devices 102, 103 connect to network 104 along with storage unit 113. Client devices, may be, for example, personal computers or network computers, handheld devices, mobile devices, tablet devices, smartphones, personal digital assistants, printing devices, recording devices, speakers, MFDs (printer/scanner/fax combinations device), etc. Computer system 200 depicted in FIG. 2 can be, for example, a client such as desktop computer 102 and/or smart phone 103 and/or another client device.

Computer system 200 can also be implemented as a server such as servers 105-111 and 114, exemplified by server 106, depending upon design considerations. In the depicted example, server 106 provides data such as boot files, operating system images, applications, and application updates to client devices 102, 103. Client devices 102, 103 and device 112 are clients to servers 105-111 and 114 in this example. Network data-processing system 100 may include additional servers, clients, and other devices not shown. Specifically, clients may connect to any member of a network of servers, which provide equivalent content. A networked computer or device 102-114 can provide a network accessible webhook or API (Application Program Interface) such that other machines can use the webhooks or APIs to remotely execute program code.

In the depicted example, network data-processing system 100 is the Internet, with network 104 representing a worldwide collection of networks and gateways that use standardized protocols, such as the Transmission Control Protocol/Internet Protocol (TCP/IP), to communicate with one another. At the heart of the internet is a backbone of high-speed data communication lines between major communications nodes, bridges, routers, and computers consisting of thousands of commercial, government, educational, and other computer systems that route data and messages. Of course, network data-processing system 100 may also be implemented as a number of different types of networks such as, for example, an intranet, a local area network (LAN), or a wide area network (WAN). FIGS. 1-3 are intended as examples and not as architectural limitations for different embodiments of the present invention.

A block diagram of a computer system 200 that executes programming for implementing parts of the methods and systems disclosed herein is shown in FIG. 2. A computing device in the form of a computer 210 configured to interface with controllers, peripheral devices, and other elements disclosed herein may include one or more processing units 202, memory 204, removable storage 212, and non-removable storage 214. Memory 204 may include volatile memory 206 and non-volatile memory 208. Computer 210 may include or have access to a computing environment that includes a variety of transitory and non-transitory computer-readable media such as volatile memory 206 and non-volatile memory 208, removable storage 212 and non-removable storage 214. Computer storage includes, for example, random access memory (RAM), read only memory (ROM), erasable programmable read-only memory (EPROM) and electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage, or other magnetic storage devices, or any other medium capable of storing computer-readable instructions as well as data including image data.

Computer 210 may include, or have access to, a computing environment that includes input 216, output 218, and a communications subsystem 220. The computer may operate in a networked environment using a communications subsystem 220 to connect to one or more remote computers, remote sensors and/or controllers, detection devices, handheld devices, multi-function devices (MFDs), speakers, mobile devices, tablet devices, mobile phones, Smartphone, or other such devices. The remote computer may also include a personal computer (PC), server, router, network PC, RFID enabled device, a peer device or other common network node, or the like. The communication connection may include a Local Area Network (LAN), a Wide Area Network (WAN), Bluetooth connection, or other networks. This functionality is described more fully in the description associated with FIG. 1.

FIG. 1 illustrates a computing environment with a person interacting with devices to view EHRs, set datum alerts, and clear datum alerts in accordance with aspects of the embodiments. The person 101 can interact with a client device such as a desktop computer 102 or smart phone 103 to set and clear datum alerts. The desktop computer 102 and smart phone 103 are connected to a communications network 104, and can therefore communicate with a variety of servers 105-111 and 114. Those servers can include a microservice server 111, an application server 110, a web server 109, a message server 108, and email server 107, an electronic health record server 105, an electronic health record datum alert server 114, or another server 106.

A client program can run on a client device such as the desktop computer 102 and access an electronic health record server 105 and an electronic health record datum alert server 114. The client program can be a purpose-built program the presents a GUI showing an EHR accessed on the electronic health record server 105, or setting/clearing datum alerts accessed on the electronic health record datum alert server 114. Alternatively, the client program can run on a server and provide a GUI displayable within a web browser. A client device can run the web browser that accesses a web server 109, the electronic health record server 105, and the electronic health record datum alert server 114 to thereby provide the EHR GUI and datum alerts to the user.

The electronic health record server 105 and the electronic health record datum alert server 114 can interact with the EHR GUI and client program to directing the attention of a person 101 to specific information via graphical user interfaces and set using a drag and drop paradigm. This processing provides an advance in computer function by interacting with an EHR to create datum alerts via dragging and dropping, and thereafter calling attention to the datum alerts. A further improvement is that the datum alerts cannot be dismissed without first being reviewed.

Output 218 is most commonly provided as a computer monitor, but may include any output device. Output 218 and/or input 216 may include a data collection apparatus associated with computer system 200. In addition, input 216, which commonly includes a computer keyboard and/or pointing device such as a computer mouse, computer track pad, touch screen, or the like, allows a user to select and instruct computer system 200. A user interface can be provided using output 218 and input 216. Output 218 may include a display 232 for displaying data and information for a user, or for interactively displaying a GUI (graphical user interface) 230. A GUI is typically responsive of user inputs entered through input 216 and typically displays images and data on display 232.

Note that the term "GUI" generally refers to a type of environment that represents programs, files, options, and so forth by means of graphically displayed icons, menus, and dialog boxes on a computer monitor screen or smart phone screen. A user can interact with the GUI to select and activate such options by directly touching the screen and/or pointing and clicking with a user input device 216 such as, for example, a pointing device such as a mouse, and/or with a keyboard. A particular item can function in the same manner to the user in all applications because the GUI provides standard software routines (e.g., program cone in application module 225 can include such software routines) to handle these elements and report the user's actions. The GUI can further be used to display the electronic health record and collection icon as discussed below.

Computer-readable instructions, for example, program code in application module 225, which can include or be representative of software routines, software subroutines, software objects, nodes, etc. described herein, are stored on a computer-readable medium and are executable by the processor device (also called a processing unit) 202 of computer 210. Application module 225 may include a computer application. A hard drive, CD-ROM, RAM, Flash Memory, and a USB drive are just some examples of articles including a computer-readable medium. The application module of FIG. 2 is illustrated as including electronic health record GUI code 234, a datum alert handler 236 and a permissions handler 238.

FIG. 3 illustrates a software system 300, which may be employed for directing the operation of the data-processing systems such as computer system 200 depicted in FIG. 2. Software application 305, may be stored in memory 204, on removable storage 212, or on non-removable storage 214 shown in FIG. 2, and generally includes and/or is associated with a kernel or operating system 310 and a shell or interface 315. One or more application programs may be "loaded" (i.e., transferred from removable storage 212 or non-removable storage 214 into the memory 204) for execution by the data-processing system 200. The application program 305 can include software components 325 such as software modules, software subroutines, software objects, electronic health record GUI handler, datum alert handler, permissions handler, etc. 325. The data-processing system 200 can receive user commands and data through interface 315, which can include input 216, output 218, and communications connections 220 accessible by a user 320 or remote device 330. These inputs may then be acted upon by the computer system 200 in accordance with instructions from operating system 310 and/or software application 305 and any software components 325 thereof.

Generally, software components 325 can include, but are not limited to, routines, subroutines, software applications, programs, objects, modules, objects (used in object-oriented programs), executable instructions, data structures, etc., that perform particular tasks or implement particular abstract data types and instructions. Moreover, those skilled in the art will appreciate that elements of the disclosed methods and systems may be practiced with other computer system configurations such as, for example, hand-held devices, mobile phones, smartphones, tablet devices, multi-processor systems, microcontrollers, printers, copiers, fax machines, multi-function devices, data networks, microprocessor-based or programmable consumer electronics, networked personal computers, minicomputers, mainframe computers, servers, medical equipment, medical devices, and the like.

Note that the terms "component," "module," or "node" as utilized herein may refer to one of or a collection of routines and data structures that perform a particular task or implements a particular abstract data type. Applications and components may be composed of two parts: an interface, which lists the constants, data types, variables, and routines that can be accessed by other modules or routines; and an implementation, which is typically private (accessible only to within the application or component) and which includes source code that actually implements the routines in the application or component. The terms application or component may also simply refer to an application such as a computer program designed to assist in the performance of a specific task such as word processing, accounting, inventory management. Components can be built or realized as special purpose hardware components designed to equivalently assist in the performance of a task.

The interface 315 can include a graphical user interface 230 that can display results, whereupon a user 320 or remote device 330 may supply additional inputs or terminate a particular session. In some embodiments, operating system 310 and GUI 230 can be implemented in the context of a "windows" system. It can be appreciated, of course, that other types of systems are possible. For example, rather than a traditional "windows" system, other operation systems such as, for example, a real-time operating system (RTOS) more commonly employed in wireless systems may also be employed with respect to operating system 310 and interface 315. The software application 305 can include, for example, software components 325, which can include instructions for carrying out steps or logical operations such as those shown and described herein.

The description herein is presented with respect to embodiments that can be embodied in the context of, or require the use of, a data-processing system such as computer system 200, in conjunction with program code in application module 225, software system 300, or data-processing system 100 and network 104 depicted in FIGS. 1-3. The disclosed embodiments, however, are not limited to any particular application or any particular environment. Instead, those skilled in the art will find that the system and method of the present invention may be advantageously applied to a variety of system and application software including database management systems, word processors, and the like. Moreover, the present invention may be embodied on a variety of different platforms including Windows, Macintosh, UNIX, LINUX, Android, Arduino, and the like. Therefore, the descriptions of the exemplary embodiments, which follow, are for purposes of illustration and not considered a limitation.

Computer systems 200 and software systems can take the form of or run as virtual machines (VMs) or containers that run on physical machines. A VM or container typically supplies an operating environment, appearing to be an operating system, to program code in an application module 225 and software applications 325 running in the VM or container. A single physical computer can run a collection of VMs and containers. In fact, the entire network data processing system 100 (but likely excluding device 112) with client devices 102-103, servers 105-111, storage 113, and network 104 all virtualized and running within a single computer (or a few computers) running VMs or containers. Those practiced in cloud computing are practiced in the use of VMs, containers, virtualized networks, and related technologies.

Figure 4:
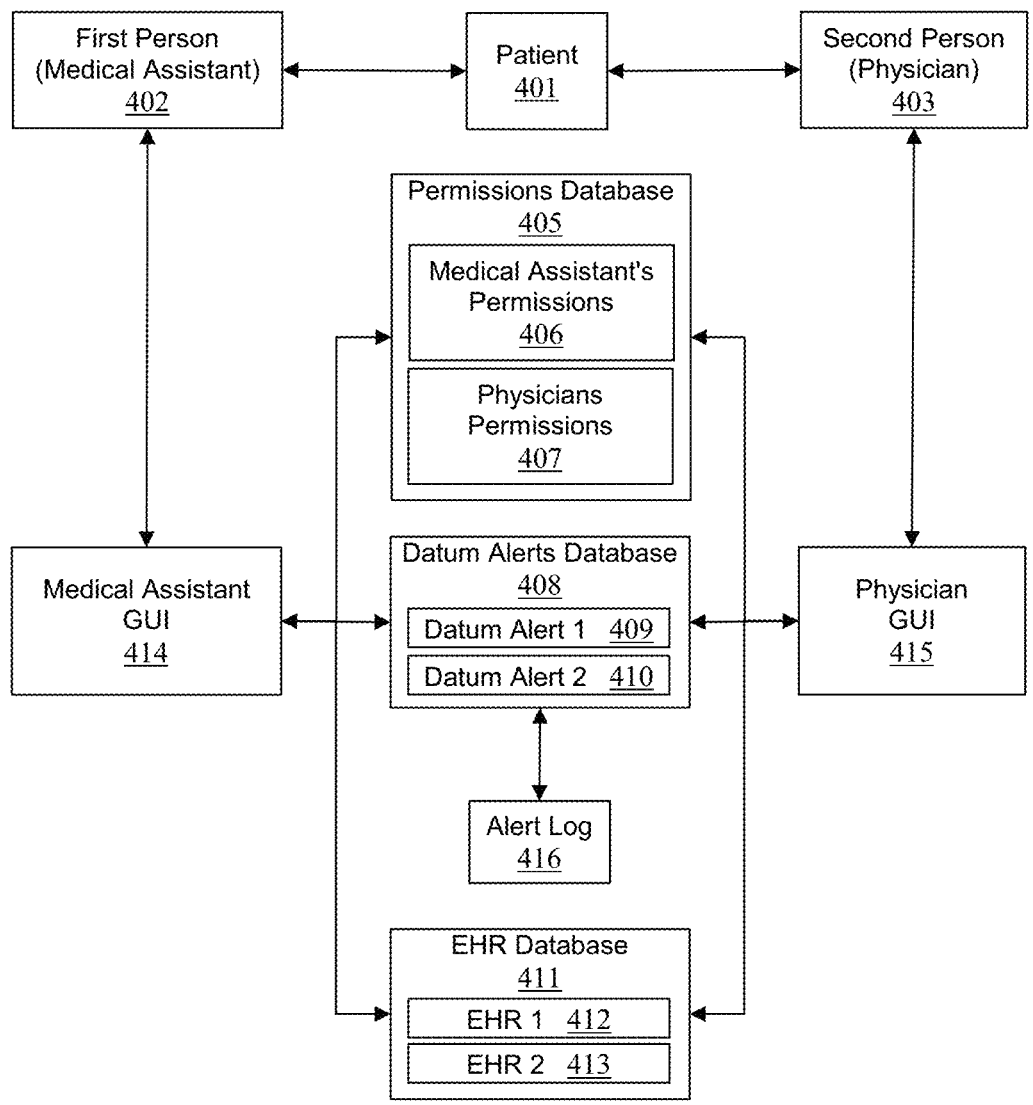
FIG. 4 illustrates a high-level block diagram of a first person setting datum alerts and a second person clearing datum alerts in accordance with aspects of the embodiments.
Figure 5:
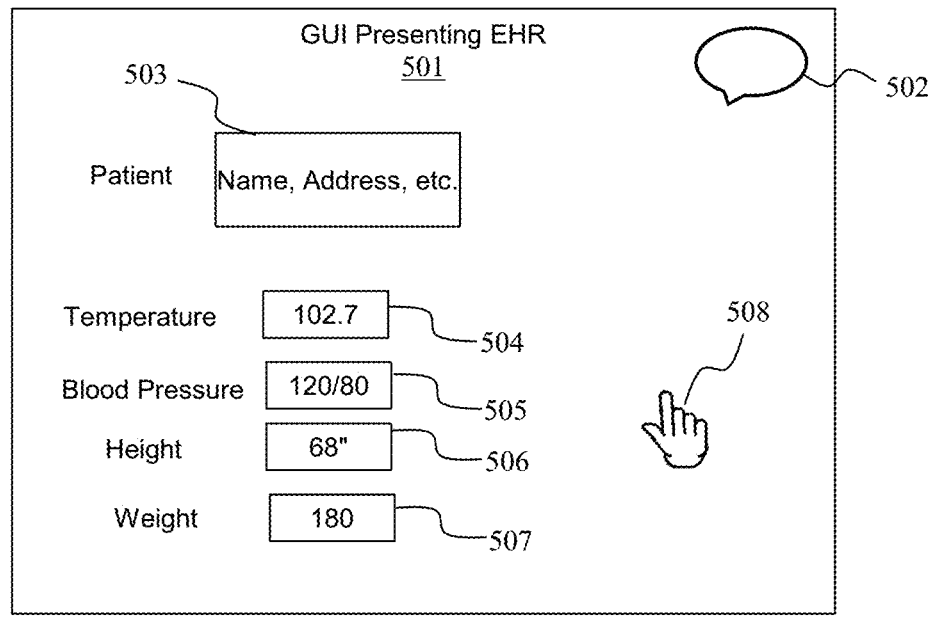
FIGS. 5-9 illustrates a GUI showing an EHR as a person drags and drops a datum to thereby associate a datum alert with the datum in accordance with aspects of the embodiments.

FIG. 4 illustrates a high-level block diagram of a first person 402 setting datum alerts 409, 410 and a second person 403 clearing datum alerts 409, 410 in accordance with aspects of the embodiments. A medical assistant (MA) 402 and a physician 403 can interact with a patient 401. The MA 402 may notice aspects of the patient's health that should be reviewed by the physician 403. The MA 402 can operate MA GUI 414 to set datum alerts 409, 410. The datum alerts can be stored in a datum alerts database 408 that is configured for recording a plurality of datum alerts in association with a plurality of electronic health record datums. The MA GUI can access an EHR database 411 to obtain an EHR 412, 413 for presentation to the MA 402. As seen below, the MA can drag EHR datums to a collection icon to thereby set a datum alert. A datum alert can be set by associating it with a datum in an EHR.

The physician 403 can operate a physician GUI 415 to clear datum alerts. The physician GUI 415 and the MA GUI 414 may be different instances of the same GUI. The physician 403 can operate physician GUI 415 to clear datum alerts 409, 410. The datum alerts can be stored in a datum alerts database 408. The physician GUI 415 can access an EHR database 411 to obtain an EHR 412, 413 for presentation to the physician 403. As seen below, the physician can clear datum alerts.

Permissions database can store data restricting the actions that the MA 402 and physician 403 can take with respect to EHRs 412, 413 and datum alerts 409, 410. An alert log 416 can log all actions on datum alerts or on datum alert database 408. By being separate from the datum alert database 408, the alert log 416 can securely record database transactions to detect tampering, to reconstruct the database, or to analyze activity.

FIGS. 5-9 illustrates a GUI 501 showing an EHR as a person drags and drops a datum to thereby associate a datum alert with the datum in accordance with aspects of the embodiments. The EHR GUI 501 presents data from an EHR. The EHR GUI may display only a portion of the EHR data as required by present needs. For example, a single intake sheet can be a tiny portion of a patient's entire EHR. The GUI may present the intake sheet and the MA 402 may fill out the intake sheet with the patients identifying information (name address, etc.) 503, temperature 504, blood pressure 505, height 506, and weight 507. The MA 402 notices that the patient has a fever and needs to ensure that the physician 403 notices and considers the patient's temperature. The patient's temperature 504 is a datum in the EHR. The MA can select the temperature (by touching a touchscreen or pressing a mouse button) and begin dragging the datum 504 toward the collection icon 502. The hand icon 508 indicates the MA's touch position or cursor position.

Figure 6:
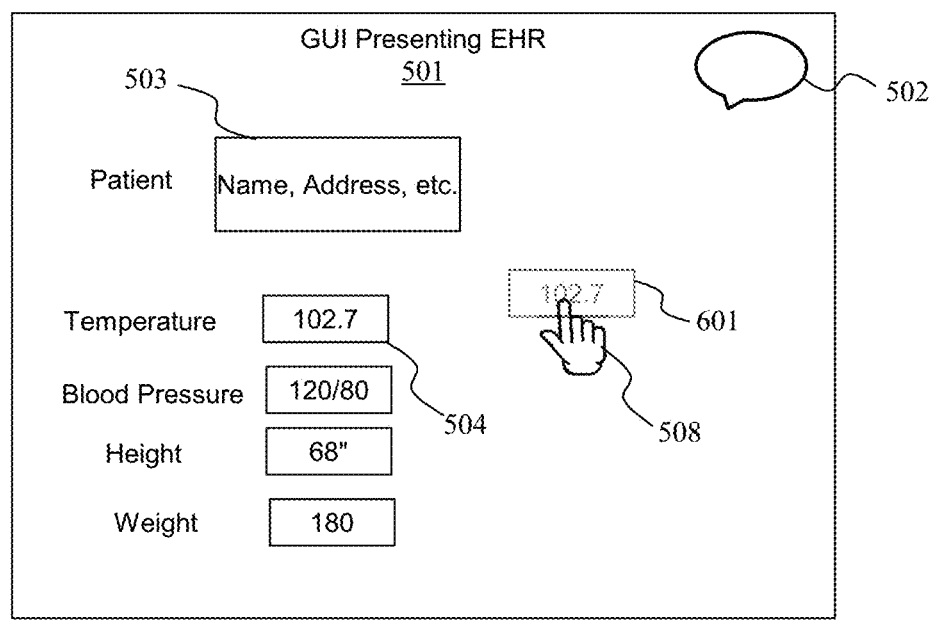
Figure 7:
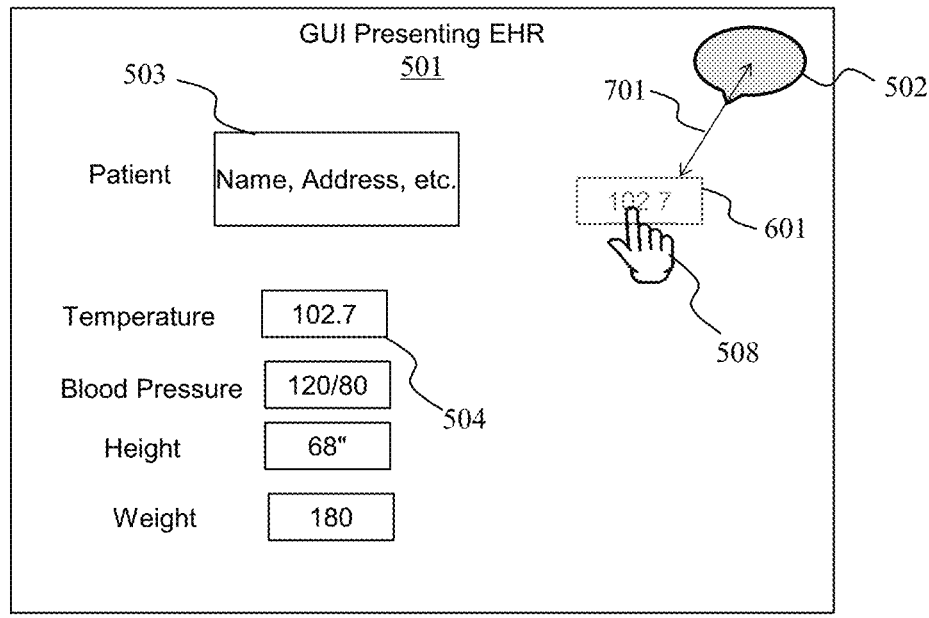

FIG. 6 shows a dragged datum 601 as the MA drags the datum 504 toward the collection icon 502. FIG. 507 shows the collection icon 502 being highlighted when the datum 504 is dragged within the collection range of the collection icon 502. The datum 54 is within the collection range of the collection icon 502 when the dragged datum 601 is within a predetermined distance 701 of the collection icon 502. There are many ways to highlight an icon, datum, or datum alert including shading (as shown in FIG. 7), changing color, flashing (making the item disappear and reappear), thickening an outline, adding a background pattern, etc. The collection icon 502 is highlighted as a signal to the MA 402 that releasing (releasing mouse button, removing finger from touch screen, etc.) the datum 504 will set a datum alert. The datum alert can be set by associating the datum alert with the datum 504.

Figure 8:
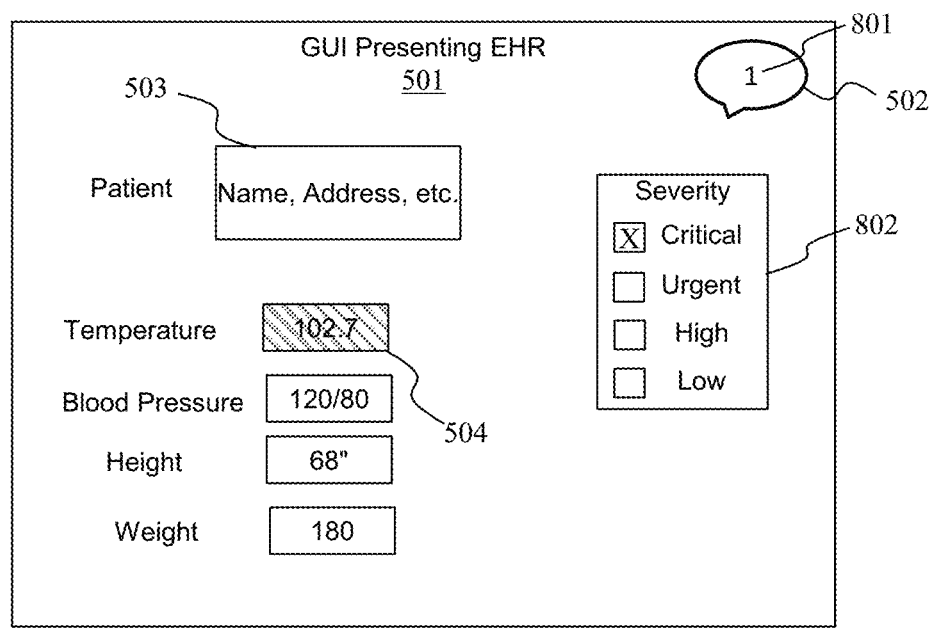
Figure 9:
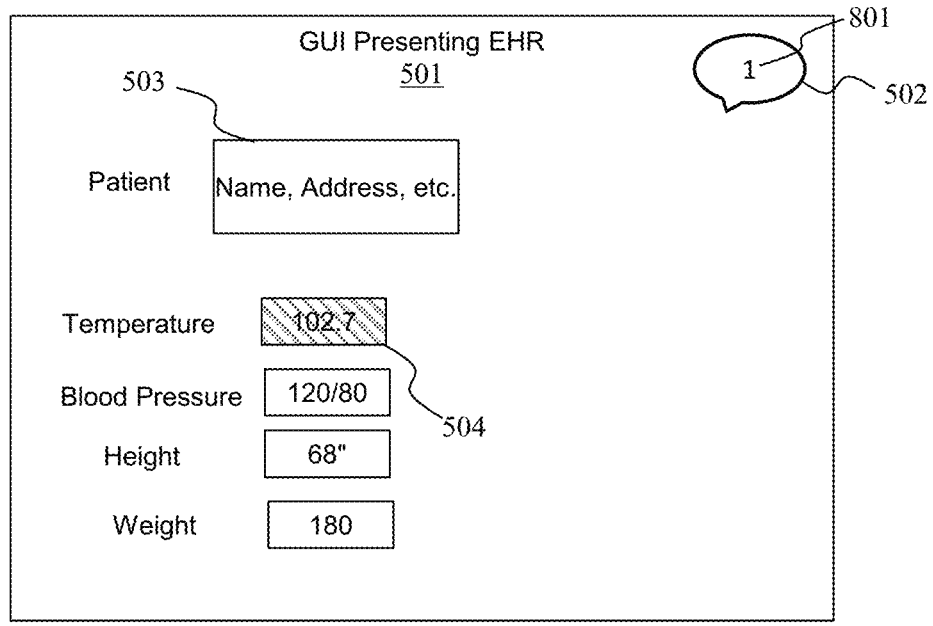

FIG. 8 shows the MA 402 selecting a "critical" severity level for the datum alert. Upon releasing the datum 504, the EHR GUI 501 can present a severity selection graphic 802. Using the severity selection graphic 802, the MA 402 can select a severity level for the datum alert. The collection icon 502 now shows a number 801 indicating that there is one datum alert to be reviewed. FIG. 9 shows the EHR GUI 501 after the datum alert is set and the severity level selected. The datum 504 is highlighted to show that there is a datum alert associated with the datum 504.

Figure 10:
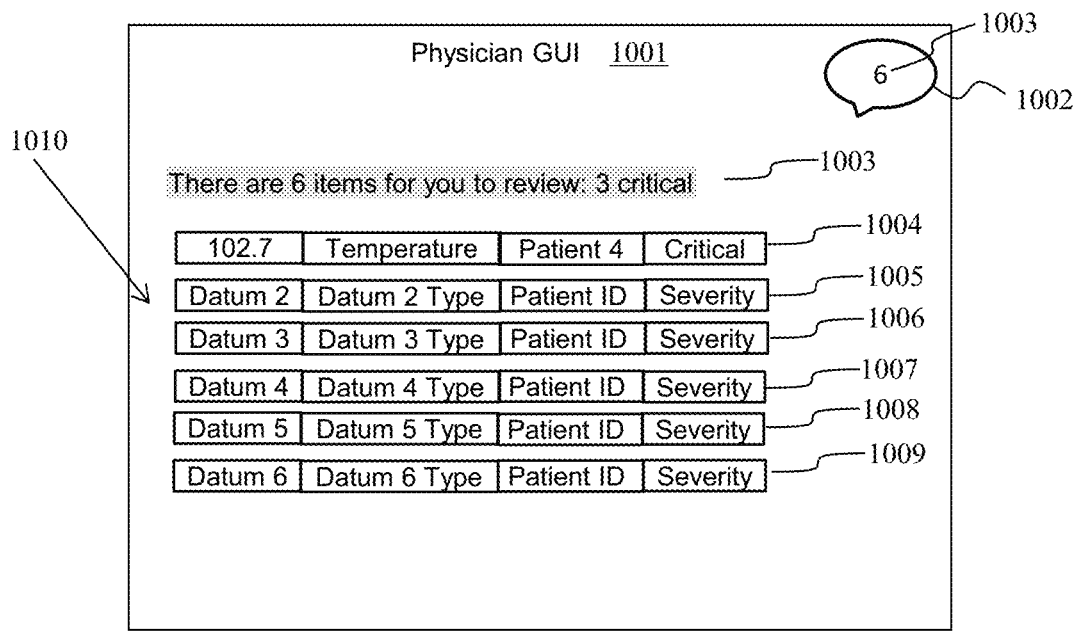
FIG. 10 illustrates a GUI presenting a list of datum alerts in accordance with aspects of the embodiments.

FIG. 10 illustrates a GUI presenting a list of datum alerts in accordance with aspects of the embodiments. A physician 403 can use the same EHR GUI 501 as the MA 402 or can use a physician GUI 1001. The physician GUI 1001 has an indicator 1002 and a number 1003 indicating that there are 6 datum alerts to review. Another indicator 1003 indicates that there are six datum alerts to review and that three of them are critical. The physician GUI 1001 provides a list 1010 of the datum alerts 1004, 1009. The list 1010 can always be presented in the physician's GUI 1001 or can be presented in response to selecting an indicator 1002, 1003. If the physician 403 is using the same GUI as the MA 402, then the list can be presented as a graphic overlaying the EHR. Selecting a datum alert can cause the GUI to present the datum alert in the context of the EHR.

Figure 11:
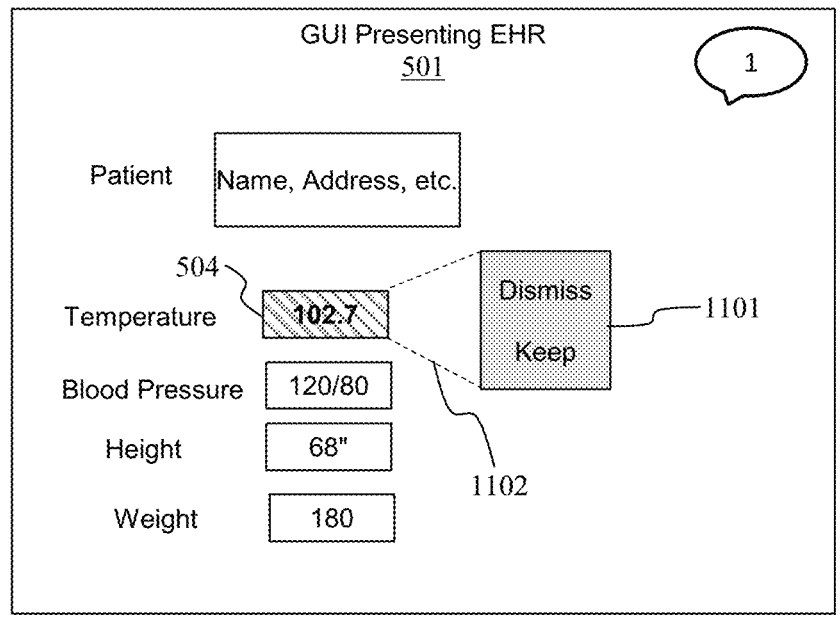
FIG. 11 illustrates dismissing a datum alert in accordance with aspects of the embodiments.

FIG. 11 shows a datum alert being presented in the context of the EHR. Here, the datum, which is the temperature "102.7" is presented with a patterned background. This non-limiting example shows the datum alert in the context of the EHR by showing the datum in the EHR in a bold font and with the patterned background. Some other type of highlighting can be used instead of or in addition to the bold font or patterned background.

FIG. 11 also illustrates dismissing a datum alert in accordance with aspects of the embodiments. Selecting the datum 504 can bring up a dismissal dialog 1101. Attention lines 1102 show that the dismissal dialog pertains to datum 504. Selecting "Dismiss" results in an alert dismissal being issued that can cause the datum alert to be cleared.

Figure 12:
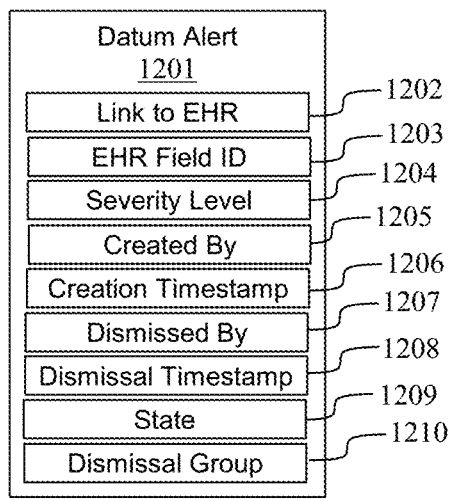
FIG. 12 illustrates a datum alert in accordance with aspects of the embodiments.

FIG. 12 illustrates a datum alert 1201 in accordance with aspects of the embodiments. The datum alert can be a data structure or database record stored in the datum alert database 408. The datum alert can include a link to an EHR 1202, an EHR field identifier 1203, the severity level 1204 of the datum alert 1201, data indicating who created or set the datum alert 1205, a timestamp indicating when the datum alert was created or set 1206, data indicating who dismissed or cleared the datum alert (if already cleared) 1207, a timestamp indicating when the datum alert was dismissed or cleared 1208, the datum alert's current state (set, cleared, . . . ) 1209, and data indicating who has permission to dismiss or clear the datum alert 1210.

Figure 13:
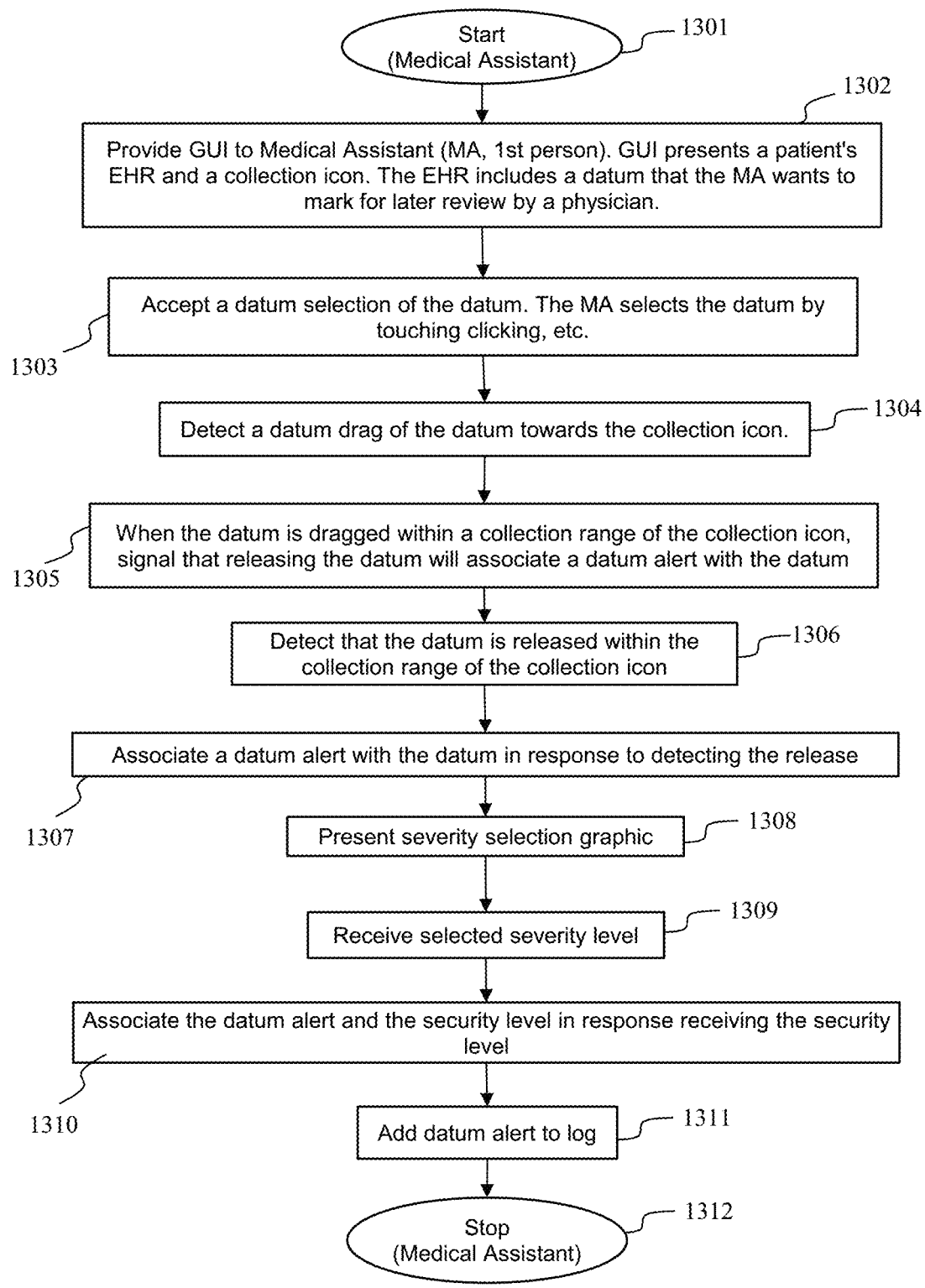
FIG. 13 illustrates a high-level flow diagram of setting a datum alert in accordance with aspects of the embodiments.

FIG. 13 illustrates a high-level flow diagram of setting a datum alert in accordance with aspects of the embodiments. After the start 1301, a GUI is provided the MA 1302. The GUI can present a patient's EHR and a collection icon. The EHR includes a datum that the MA wants to mark for later review by a physician. Accepting a datum selection 1303 occurs when the GUI detects that the MA has selected a datum by touching a touch pad, pressing a mouse button, or some other action. Detecting a datum drag 1304 occurs when the MA drags the datum. Signaling that releasing the datum will associate a datum alert with the datum 1305 occurs when the datum is dragged within a collection range of the collection icon. Upon detecting that the datum was released within the collection range of the collection icon 1306, a datum alert is associated with the datum 1307. The severity graphic is presented 1308 and a severity level received 1309. The datum alert is also associated with the security level 1310. The creation/setting of the datum alert is logged 1311 before the process stops 1312.

Figure 14:
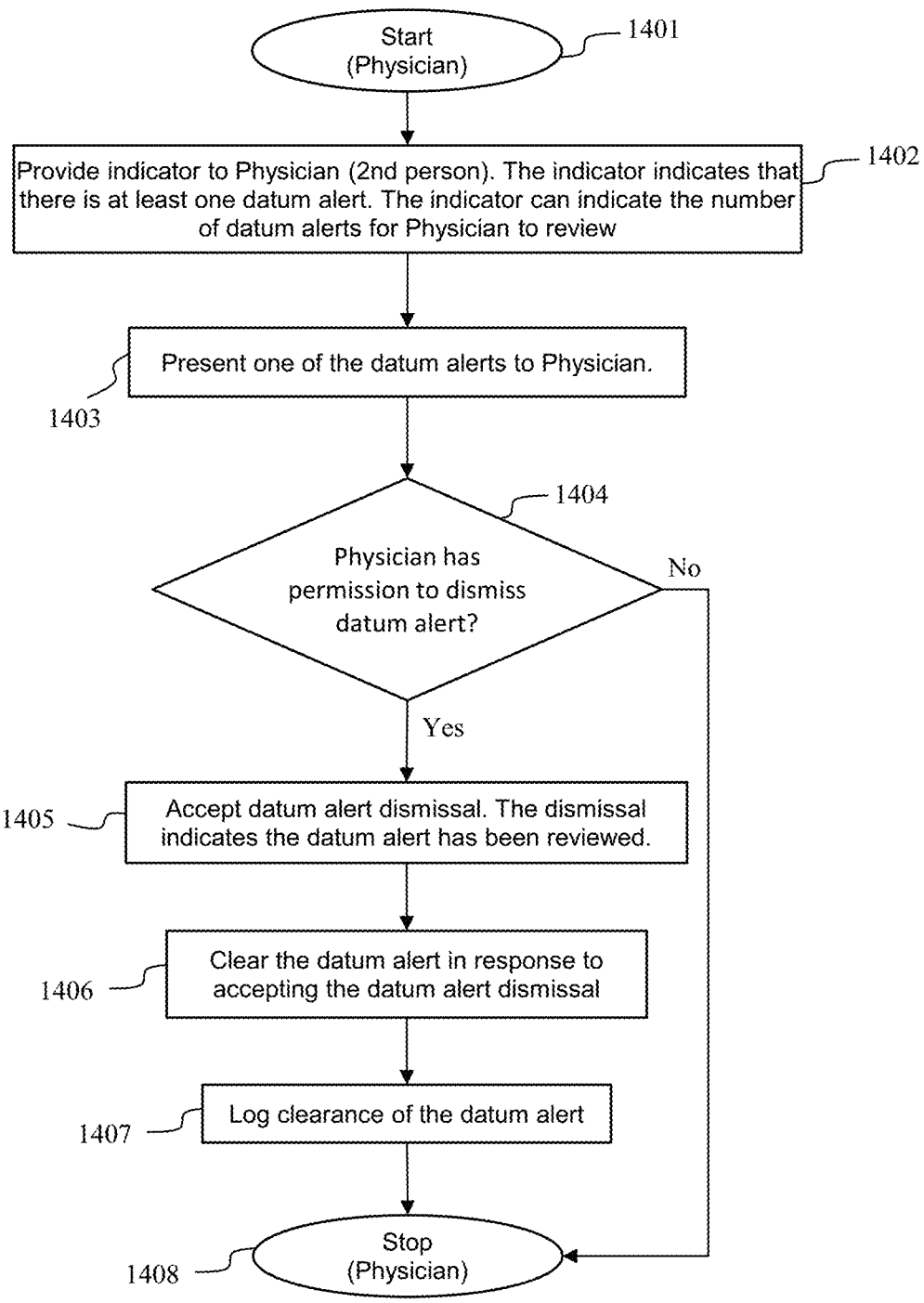
FIG. 14 illustrates a high-level flow diagram of clearing a datum alert with permission in accordance with aspects of the embodiments.

FIG. 14 illustrates a high-level flow diagram of clearing a datum alert with permission in accordance with aspects of the embodiments. After the start 1401 an indicator is provided to a physician 1402. The indicator indicates that there is at least one datum alert. The indicator can indicate the number of datum alerts for the physician to review. A datum alert is presented to the physician 1403. If the physician does not have permission to clear the datum alert 1404, the process stops 1408 without clearing the datum alert because the physician is not permissioned to submit a datum alert dismissal. If the physician has permission to clear the datum alert 1404, the datum alert dismissal is accepted 1405 because the physician is permissioned for datum alert clearing, the datum alert cleared 1406, the datum alert clearance logged 1407 before the process stops.

Figure 15:
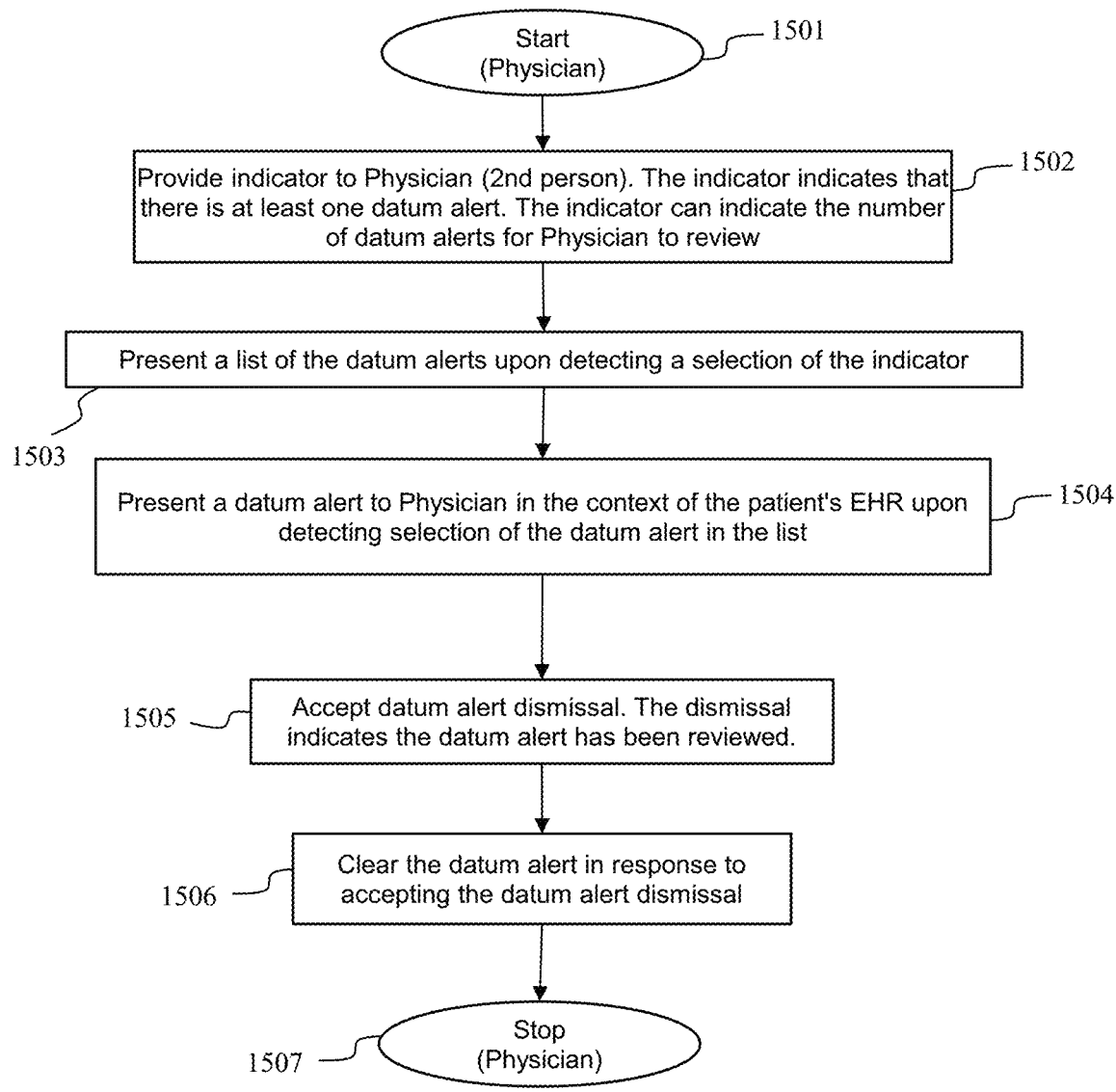
FIG. 15 illustrates a high-level flow diagram of clearing a datum alert from a list in accordance with aspects of the embodiments.

FIG. 15 illustrates a high-level flow diagram of clearing a datum alert from a list in accordance with aspects of the embodiments. After the start 1501 an indicator is provided to a physician 1502. The indicator indicates that there is at least one datum alert. The indicator can indicate the number of datum alerts for the physician to review. Upon detecting a selection of the indicator, a list of the datum alerts is presented 1503. Upon detecting selection of a datum alert in the list, the datum alert is presented to the physician in the context of the patient's EHR 1504. A datum alert dismissal is accepted 1505 and the datum alert is cleared 1506 before the process stops 1507.

Figure 16:
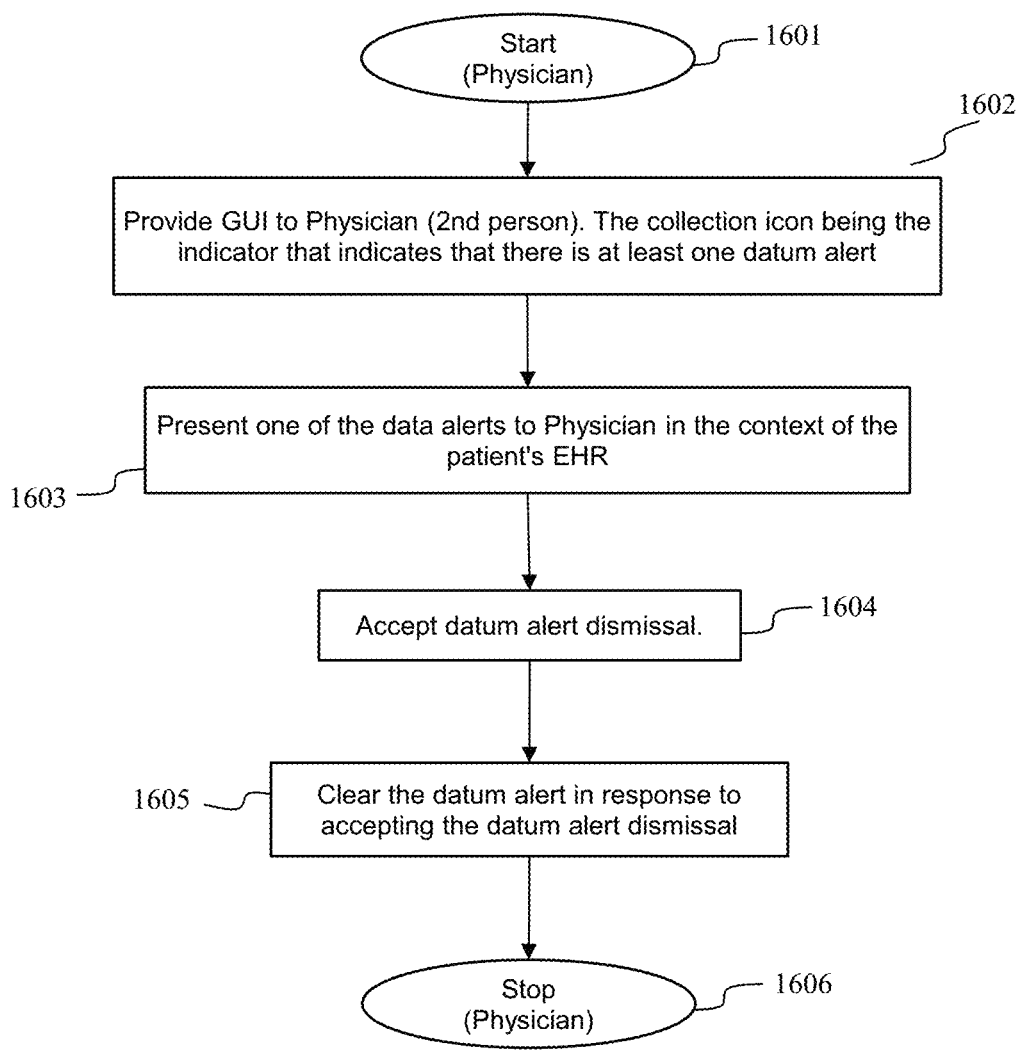
FIG. 16 illustrates a high-level flow diagram of clearing a datum alert from an EHR GUI in accordance with aspects of the embodiments.

FIG. 16 illustrates a high-level flow diagram of clearing a datum alert from an EHR GUI in accordance with aspects of the embodiments. After the start 1601, the EHR GUI (e.g. FIG. 5, element 501) is provided to the physician 1602. The collection icon indicates that there is at least one datum alter to review. A datum alert is presented to the physician in the context of the patient's EHR 1603. A datum alert dismissal is accepted 1604 and the datum alert is cleared 1605 before the process stops 1606.

The examples shown here are presented to illustrate aspects of the embodiments and are not intended to be limiting.

It will be appreciated that variations of the above-disclosed and other features and functions, or alternatives thereof, may be desirably combined into many other different systems or applications. Also, it should be understood that various presently unforeseen or unanticipated alternatives, modifications, variations or improvements therein may be subsequently made by those skilled in the art which are also intended to be encompassed by the following claims.

What is claimed is:

1. A method for marking a datum of an electronic health record for later review, comprising:
   providing graphical user interface for a first permission level and a second permission level, the graphical user interface presenting an interface window comprising a collection icon and the electronic health record comprising a plurality of datum specific to a record;
   accepting a datum selection of a portion of the plurality of datum of the electronic health record in accordance with the first permission level, the graphical user interface having presented the datum as part of the electronic health record in accordance with the first permission level;
   detecting a datum drag of the selected portion of datum toward a predetermined distance from the collection icon within the interface window;
   signaling that releasing the selected portion of datum will associate a datum alert with the datum;
   detecting a datum release while the detected datum drag is within the predetermined distance from the collection icon; and
   associating the datum alert with the selected portion of datum for the collection icon in response to detecting the datum release, wherein the datum alert is associated with the selected portion of the datum in accordance with a second permission level.

2. The method of claim 1 further comprising:
   providing an indicator in accordance with the second permission level, the indicator indicating there is at least one datum alert;
   presenting one of the at least one datum alert in accordance with the second permission level;
   accepting a datum alert dismissal of the presented one of the at least one datum alert; and
   clearing the datum alert in response to accepting the datum alert dismissal.

3. The method of claim 2 further comprising providing the graphical user interface in accordance with the second permission level, the graphical user interface presenting the collection icon and the electronic health record, the collection icon comprising the indicator.

4. The method of claim 2 wherein the indicator indicates a count of the at least one datum alert.

5. The method of claim 2 wherein selecting the indicator causes a list of the at least one datum alert to be presented.

6. The method of claim 5 wherein selecting a one of the at least one datum alert on the list causes the electronic health record to be displayed on the one of the at least one datum alert.

7. The method of claim 2 wherein the datum alert dismissal is cleared only if the second permission level has been authorized.

8. The method of claim 2 further comprising logging the datum alert and the datum alert dismissal.

9. The method of claim 2, the indicator indicating a severity level that is the highest of any severity level associated with any of the at least one datum alert.

10. The method of claim 1 further comprising:
displaying a severity selection graphic upon detecting the datum release, the severity selection graphic providing for selecting a severity level of the datum alert; and
associating the severity level with the datum alert.

11. A system for marking a datum of an electronic health record for later review, comprising:
a display device displaying a generated graphical user interface for a first permission level and a second permission level, the graphical user interface presenting an interface window comprising a collection icon and the electronic health record comprising a plurality of datum specific to a record;
an input device configured to accept a datum selection of a portion of the plurality of datum of the electronic health record in accordance with the first permission level, the graphical user interface having presented the datum as part of the electronic health record in accordance with the first permission level;
a processor operatively coupled to the display device and the input device, wherein the processor is configured to cause the display device to show the graphical user interface, wherein the processor is configured to process the datum selection;
an application module, configured to store one or more executable applications;
a memory, operatively coupled to the processor, wherein the memory is configured to store the electronic health record and the datum;
wherein the processor is configured to detect a datum drag of the selected portion of datum toward a predetermined distance from the collection icon within the interface window;
wherein the processor is configured to cause the display device to signal that releasing the selected portion of datum while the detected datum drag is within the predetermined distance from the collection icon will associate a datum alert with the datum;
wherein the processor is configured to associate the datum alert with the selected portion of datum in response a datum release, wherein the datum alert is associated with the selected portion of the datum in accordance with a second permission level.

12. The system of claim 11,
wherein the processor is configured to provide an indicator in accordance with the second permission level, the indicator indicating there is at least one datum alert;
wherein the processor is configured to cause the display device to present one of the at least one datum alert in accordance with the second permission level; and
wherein the processor is configured to clear the datum alert in response to accepting a dismissal of the presented one of the at least one datum alert.

13. The system of claim 12 wherein the processor is configured to provide the graphical user interface in accordance with the second permission level, the graphical user interface presenting the collection icon and the electronic health record, the collection icon comprising the indicator.

14. The system of claim 12 wherein the indicator indicates a count of the at least one datum alert, wherein selecting the indicator causes a list of the at least one datum alert to be presented, wherein selecting a one of the at least one datum alert on the list causes the electronic health record to be displayed and centered on the one of the at least one datum alert, and wherein the processor is configured to cause the graphical user interface to highlight the datum associated with the datum alert.

15. The system of claim 12 wherein the datum alert dismissal is accepted only if the second permission level has been authorized.

16. The system of claim 12,
wherein the processor is configured to, upon detecting the datum release, cause the graphical user interface to display a severity selection graphic that provides for selecting a severity level for the datum alert;
wherein the processor is configured to associate the datum alert with the severity level; and
wherein the indicator indicates the severity level associated with one of the at least one datum alert.

17. A method for marking a plurality of electronic health record datums for later review, comprising:
providing graphical user interface for a first permission level and a second permission level, the graphical user interface presenting an interface window comprising a collection icon and an electronic health record of a patient comprising a plurality of datum specific to a record;
highlighting the collection icon in response to detecting that one of the plurality of electronic health record datums has been dragged within the interface window from the electronic health record and is within a collection range of the collection icon in accordance with the first permission level;
recording in a database a plurality of datum alerts associated with the plurality of electronic health record datums for the collection icon, wherein each of the plurality of datum alerts is associated with one of the plurality of electronic health record datums that was dragged and released within the collection range of the collection icon, wherein the datum alert is associated with the selected portion of the datum in accordance with a second permission level.

18. The method of claim 17 further comprising:
providing the graphical user interface in accordance with the second permission level, the collection icon indicating a count of the plurality of datum alerts;
presenting one of the plurality of datum alerts in accordance with the second permission level within the electronic health record;
providing the second permission level with the ability to clear the one of the plurality of datum alerts only if the second person is permissioned for datum alert clearing;
accepting a datum alert dismissal for the one of the plurality of datum alerts; and
clearing the one of the plurality of datum alerts in response to receiving the datum alert dismissal for the one of the plurality of datum alerts.

19. The method of claim 18 further comprising:
providing for the first permission level to associate a severity level with each of the plurality of datum alerts, wherein the collection icon indicates the severity level that is a highest of any severity level associated with any of the plurality of datum alerts.

20. The method of claim 19 wherein the collection icon indicates a number of the plurality of datum alerts having the severity level that is the highest of any severity level associated with any of the plurality of datum alerts.

\* \* \* \* \*